United States Patent [19]

Burckhardt et al.

[11] 4,190,604

[45] Feb. 26, 1980

[54] PROCESS FOR PRODUCING DESOXY-α-ACIDS

[75] Inventors: Urs Burckhardt, Basel; Richard J. Troxler, Birsfelden, both of Switzerland

[73] Assignee: Ciba-Geigy Corporation, Ardsley, N.Y.

[21] Appl. No.: 934,129

[22] Filed: Aug. 16, 1978

[51] Int. Cl.² ............................................. C07C 45/00
[52] U.S. Cl. .................................... 260/592; 560/231
[58] Field of Search ......................... 260/592, 586 D; 562/231

[56] References Cited

U.S. PATENT DOCUMENTS

| | | | |
|---|---|---|---|
| 4,053,517 | 10/1977 | Reininger et al. | 260/592 |
| 4,101,585 | 7/1978 | Burckhardt et al. | 260/592 |

OTHER PUBLICATIONS

Verzele, Eur. Brew Conv. Proc. Congr., 1971, 14, pp. 95–106.
Stevens, Chem. Revs., 67, pp. 19–71 (1967).

*Primary Examiner*—James H. Reamer
*Attorney, Agent, or Firm*—Harry Falber

[57] ABSTRACT

A process for the production of desoxy-α-acids from the corresponding β-acids is disclosed which process comprises converting a β-acid into a mixture of its monoacylation products and subsequently reacting the monoacylation product at 160° to 250° C., in the presence of a lower alkanoic acid with an anhydride of such an alkanoic acid, with the splitting-off of isoprene, to obtain the triacyl derivative of the corresponding desoxy-α-acid, and hydrolysing said triacyl derivative to obtain the desoxy-α-acid. Desoxy-α-acids are valuable intermediates for producing bitter principles, which are used in the foodstuffs and drinks industry.

5 Claims, No Drawings

PROCESS FOR PRODUCING DESOXY-α-ACIDS

The present invention relates to a process for producing desoxy-α-acids of the formula I

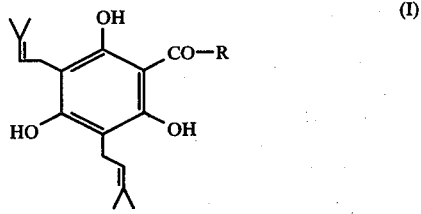

in which
R represents a straight-chain or branched-chain alkyl group having 1 to 5 carbon atoms.

The dexosy-α-acids of the formula I (desoxyhumulons) are valuable intermediates for producing bitter principles, which are used in the foodstuffs and drinks industry particularly for producing beer. The desoxy-α-acids of the formula I can be converted by oxidation into α-acids (humulons), which are identical to the bitter principles occurring in hop resin. These α-acids are converted in the brewing process into iso-α-acids (isohumulons), which are responsible for the specific bitter taste of the beer. The isoα-acids can be produced however synthetically by isomerization of α-acids.

The conversion of desoxy-α-acids into α-acids and the isomerization thereof to give iso-α-acids can be described by formulae as follows:

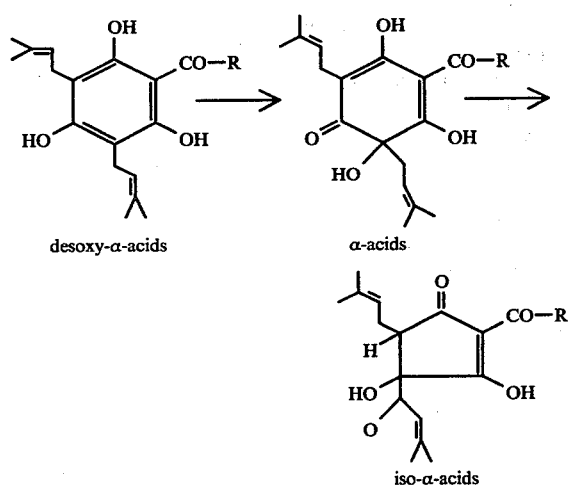

desoxy-α-acids        α-acids iso-α-acids

Dried hops contain about 15 per cent by weight of resins which consist partly of α-acids and partly of β-acids (lupulons) of the formula

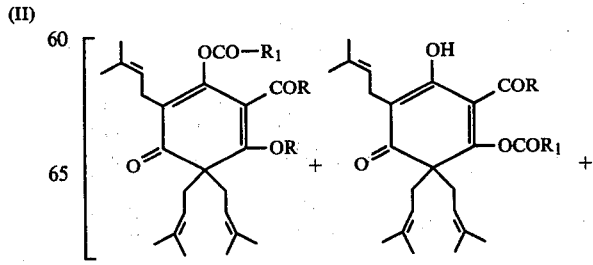
(II)

in which R has the meaning given under the formula I, with the β-acids frequently predominating quantitatively. In contrast to to the α-acids, these β-acids are not bitter principles and are also not converted in the brewing process into bitter principles. They are present in the unchanged form in the filtration residues of the brewing process, and can be recovered from these residues by extraction.

β-Acids occur also as by-products in the production of desoxy-α-acids by prenylation of acylphloroglucinols. Furthermore, β-acids can be obtained by extraction of dried hops and subsequent separation of the resulting mixture consisting of α-and β-acids (see Eur. Brew. Conv. Proc. Congr. 1971, 14, 105–106).

In connection with the brewing of beer, the only possibility of utilising these β-acids hitherto has been to convert them by oxidation into the hulupons which can be used as bitter principles. These hulupons possess however the desired bitter taste to a much lesser extent than do the α-acids of the iso-α-acids which can be produced from the α-acids.

The object of the present invention is therefore to provide a process by which the β-acids can be converted in a simple manner into desoxy-α-acids of the formula I, which in their turn, as already stated, can be transformed into the α-acids or iso-α-acids which can be used as bitter principles.

The process according to the invention comprises converting a β-acid of the formula II

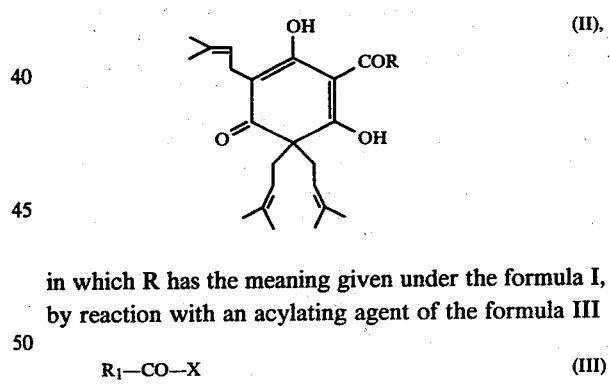

in which R has the meaning given under the formula I, by reaction with an acylating agent of the formula III $$R_1-CO-X \qquad (III)$$

in which $R_1$ represents an alkyl group having 1 to 3 carbon atoms, and X represents chlorine, bromine or a group $R_1-CO-O-$, in the presence of a base, into a mixture of monoacylation products of the formula IV -continued

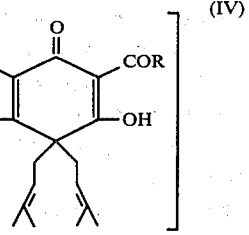

(IV)

in which R and $R_1$ have the meanings given under the formula I; subsequently reacting this monoacylation product at 160° to 250° C., in the presence of a carboxylic acid of the formula V $R_1COOH$ (V), in which $R_1$, has the meaning given above, with an anhydride of such a carboxylic acid, with the splitting-off of isoprene, to give a triacyl compound of the formula VI

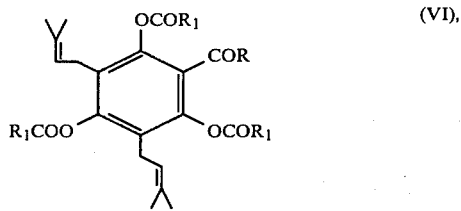

(VI), in which R and $R_1$ have the aforesaid meanings; and then hydrolysing this compound to yield a desoxy-α-acid of the formula I.

Suitable acylating agents for the monoacylation reaction are carboxylic acid chlorides and carboxylic acid bromides and also carboxylic acid anhydrides. The reaction of acid halides of the formula III with β-acids of the formula II is advantageously performed in a solvent, for example in an ether such as tetrahydrofuran, or ethylene glycol dialkyl ether such as ethylene glycol dimethyl ether, at temperatures between 0° and 50° C., preferably between 20° and 30° C., in the presence of a base, for example an alkali metal hydroxide, such as sodium hydroxide or potassium hydroxide, or an alkali metal hydride such as sodium hydride or potassium hydride. The reaction of an acid anhydride of the formula III with a β-acid of the formula II, which is the preferred method for producing the monoacylation products of the formula IV, is performed advantageously in the presence of excess anhydride as solvent, and in the presence of an alkali metal salt of the corresponding carboxylic acid at temperatures between 50° and 150° C., preferably between 100° and 120° C. Suitable acid halides and acid anhydrides are for example the chloride, bromides and anhydrides of acetic acid, propionic acid, butyric acid and isobutyric acid. Preferred acylating agents for the monoacylation of β-acids of the formula II are acetyl chloride and acetic anhydride.

The monoacylation product of the formula IV can be isolated by removal of the solvent by evaporation, and purified by column-chromatography, for example with chloroform on silica gel 60.

The resulting monoacylation product of the formula IV is subsequently converted at 160° to 250° C., in the presence of a carboxylic acid of the formula V, with the anhydride of the formula III, with the splitting-off of isoprene, into a triacyl compound of the formula VI. This reaction is advantageously performed in an excess of the anhydride, which is used for acylation, as solvent. Suitable anhydrides are acetic acid anhydride, propionic acid anhydride and butyric acid anhydride. The preferred anhydride amongst these is acetic acid anhydride.

The carboxylic acid of the formula V is added in amounts of 0.1 to 10 percent by weight, relative to the amount of anhydride used, to the reaction mixture. It is advantageous to use the carboxylic acid corresponding to the employed anhydride. Suitable carboxylic acids, which can be used in admixture with their anhydrides, are acetic acid, propionic acid, butyric acid and isobutyric acid. A mixture of acetic acid and acetic anhydride is preferably used.

In order to attain the reaction temperatures given above, the reaction of the monoacylation products of the formula IV with the anhydride of a carboxylic acid of the formula V is advantageously performed in a closed system, for example in a bomb tube or in an autoclave, under pressure. Depending on the nature of the mixture of carboxylic acid and carboxylic anhydride and on the temperature applied, there is established a pressure of 2 to 20 bars.

The triacyl compound of the formula VI can be isolated by distilling off the excess anhydride and the carboxylic acid from the reaction mixture. The crude product thus obtained can be purified, for example by chromatography with chloroform on silica gel 60, before the final hydrolysis of the triazyl compound of the fomrula VI. Preferably, however, the crude product is hydrolysed directly by the addition of aqueous alkali, for example aqueous sodium hydroxide solution or aqueous potassium hydroxide solution, at 0° to 50° C., preferably at 20° to 30° C. In order to remove formed chromans, the alkaline solution obtained is extracted with a solvent immiscible with water, for example with methylene chloride, chloroform, carbon tetrachloride, benzene, toluene or ether. After removal of the chromans, the solution is acidified by the addition of a mineral acid, for example hydrochloric acid or sulfuric acid, and again extracted with one of the aforementioned solvents. From the extract dried over sodium sulfate is then obtained, by evaporating off the solvent, the crude desoxy-α-acid of the formula I. This can be purified by crystallisation or by chromatography for example with chloroform on silica gel 60.

It is possible by the process according to the invention to convert in a simple manner both naturally occurring and synthetically produced β-acids of the formula II into the corresponding desoxy-α-acids of the formula I. The extract obtained from hops can in this manner be utilised to an extent greater than that hitherto possible for the production of the iso-α-acids used as bitter principles. The process according to the invention is suitable in particular for producing desoxy-n-humulons.

The process according to the invention is further illustrated by the Examples which follow.

EXAMPLE 1

Production of monoacyllupulons (a) Acetyl-n-lupulon 2.7 g of a 55% oily sodium hydride suspension is introduced, with stirring, into a solution of 12.45 g (0.03 mol) of n-lupulon in 100 ml of ethylene glycol dimethyl ether. There is subsequently added dropwise at 0° C. 4.8 g (0.06 mol) of acetyl chloride, and the reaction mixture turns yellowish-green. After the acetyl chloride has been added, the temperature is allowed to rise to 20° to 25° C., and stirring is continued for 2 ½ hours. The whole of the mixture is subsequently poured into 200 g of a mixture of ice and hydrochloric acid, and extracted three times with 150 ml of ether each time. The combined ether extracts are washed twice with 50 ml of 2 N hydrochloric acid and twice with 50 ml of deionised water, and dried with sodium sulphate. The ether is evaporated off in vacuo to leave 21.0 g of crude acetyl-n-lupulon in the form of red oil. The crude product is purified by chromatography on 2 kg of silica gel 60 with chloroform as the eluant to yield 9.1 g (65% of theory) of pure acetyl-n-lupulon.

(b) Acetyl-n-lupulon

A solution of 1.0 g (2.4 mmol) of n-lupulon and 0.1 g of sodium acetate in 20 ml of acetic anhydride is heated under nitrogen in the course of 5 minutes to 100° C., and held for a further 15 minutes at 100° to 115° C. The reaction mixture is then allowed to cool, and the unreacted acetic anhydride is distilled off at 20 Torr. The residue is chromatographed on 300 g of silica gel 60 with chloroform as the eluant to yield 1.0 g (90% of theory) of pure acetyl-n-lupulon.

EXAMPLE 2

Production of 4-n-desoxyhumulon 1.1 g (2.4 mmols) of acetyl-n-lupulon, 20 ml of acetic anhydride and 0.3 ml of acetic acid are stirred in an autoclave for 5 hours at 200° C. The unreacted acetic anhydride and the formed acetic acid are subsequently distilled off in vacuo. As residue is obtained 1.5 g of crude triacetoxy-4-desoxyhumulon in the form of dark oil. To the crude product is added 20 ml of 2 N sodium hydroxide solution, and stirring is maintained for 24 hours under nitrogen at room temperature. The alkaline reaction mixture is then extracted twice with 50 ml of ether each time. The ether is evaporated off from the extract to leave 0.7 g of a mixture of various chromans. The alkaline residual solution is acidified with 2 N hydrochloric acid, and extracted three times with 50 ml of ether each time. The combined extracts are dried over sodium sulphate, and the ether is evaporated off to leave 0.5 g of crude 4-n-desoxyhumulon in the form of oil. The crude product is chromatographed on 100 g of silica gel 60 with chloroform as the eluant to yield 0.2 g (24% of theory) of pure 4-n-desoxyhumulon having a melting point of 68° to 72° C.

EXAMPLE 3

Production of 4-n-desoxyhumulon 1.0 g (2.1 mmol) of triacetoxy-4-desoxyhumulon and 15 ml of 2 N sodium hydroxide solution are stirred for 5 hours at room temperature. The resulting clear, yellowish-orange solution is neutralised with 15 ml of 2 N hydrochloric acid, and subsequently extracted three times with 20 ml of ether each time. The combined ethereal extracts are dried over sodium sulphate, and the ether is subsequently evaporated off to leave 0.76 g (95% of theory) of 4-n-desoxyhumulon having a melting point of 74° to 78° C.

We claim:

1. A process for producing desoxy-α-acids of the formula I

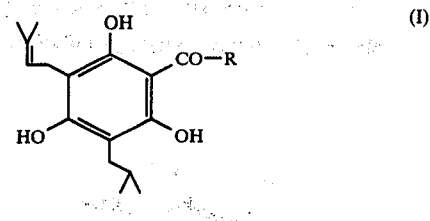

in which

R represents a straight-chain or branched-chain alkyl group having 1 to 5 carbon atoms, which process comprises converting a β-acid of the formula II

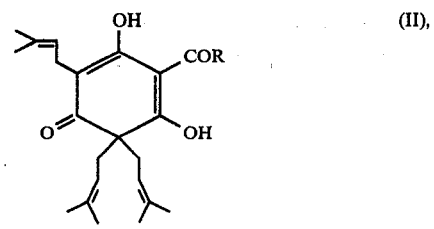

in which R has the meaning given under the formula I, by reaction with an acylating agent of the formula III $$R_1\text{—CO—X} \qquad (III)$$

in which $R_1$ represents an alkyl group having 1 to 3 carbon atoms, and X represents chlorine, bromine or a group $R_1$—CO—O—, at a temperature of from 0°–50° C. when X is chlorine or bromine and at a temperature of from 50°–150° C. when X is $R_1$—CO—O, in the presence of a base, into a mixture of monoacylation products of the formula IV

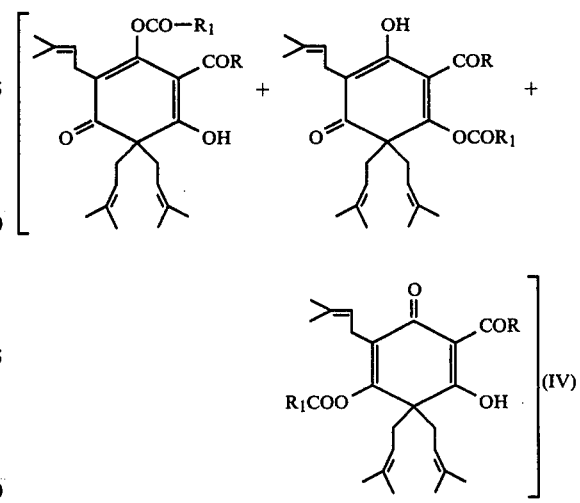

in which R and $R_1$ have the meanings given under the formulae I and III; subsequently reacting this monoacylation product at 160° to 250° C., in the presence of from 0.1–10%, by weight of anhydride, of a carboxylic acid of the formula V $$R_1COOH \quad (V),$$

in which $R_1$ has the meaning given above, with an anhydride of such a carboxylic acid, with the splitting-off of isoprene, to give a triacyl compound of the formula VI

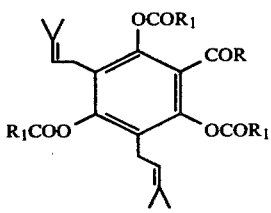 (VI), in which R and $R_1$ have the aforesaid meanings; and then hydrolysing this compound at a temperature of from 0°–50° C. with aqueous alkali to yield a desoxy-α-acid of the formula I.

2. A process according to claim 1, in which the monoacylation of β-acids of the formula II is performed at temperatures between 0° and 50° C. in the present of a solvent.

3. A process according to claim 1, in which the monoacylation of a β-acid of the formula II with an acid anhydride of the formula III is performed in the presence of excess anhydride as solvent, and in the presence of an alkali metal salt of the corresponding carboxylic acid at temperatures between 50° and 150° C.

4. A process according to claim 1, in which the reaction of the monoacylation product of the formula IV is performed in the presence of excess anhydride as solvent.

5. A process according to claim 1, in which the reaction of the monoacylation product of the formula IV with the anhydride of a carboxylic acid of the formula V is performed under pressure in a closed system.

* * * * *